United States Patent
Ando

(10) Patent No.: US 10,829,599 B2
(45) Date of Patent: Nov. 10, 2020

(54) ORGANOSILICONE EMULSION COMPOSITION

(71) Applicant: Shin-Etsu Chemical Co., Ltd., Tokyo (JP)

(72) Inventor: Yuji Ando, Annaka (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 95 days.

(21) Appl. No.: 16/000,051

(22) Filed: Jun. 5, 2018

(65) Prior Publication Data

US 2018/0346661 A1 Dec. 6, 2018

(30) Foreign Application Priority Data

Jun. 6, 2017 (JP) .................... 2017-111487

(51) Int. Cl.
| | |
|---|---|
| *C08L 83/04* | (2006.01) |
| *C08J 3/05* | (2006.01) |
| *C08G 77/02* | (2006.01) |
| *C09D 183/04* | (2006.01) |
| *C08G 77/18* | (2006.01) |
| *C08G 77/46* | (2006.01) |
| *A61K 8/06* | (2006.01) |
| *A61K 8/894* | (2006.01) |

(52) U.S. Cl.
CPC .............. *C08J 3/05* (2013.01); *C08L 83/04* (2013.01); *A61K 8/06* (2013.01); *A61K 8/894* (2013.01); *C08G 77/02* (2013.01); *C08G 77/18* (2013.01); *C08G 77/46* (2013.01); *C08J 2383/04* (2013.01); *C08J 2383/06* (2013.01); *C09D 183/04* (2013.01)

(58) Field of Classification Search
CPC ......... C08L 83/04; C08J 2383/06; C08J 3/05; A61K 8/06; A61K 8/894
See application file for complete search history.

(56) References Cited

U.S. PATENT DOCUMENTS

| | | | |
|---|---|---|---|
| 4,814,376 A | 3/1989 | Tanaka et al. | |
| 4,961,877 A * | 10/1990 | Shimizu | B01D 19/0409 516/118 |
| 5,684,112 A * | 11/1997 | Berthiaume | A61K 8/585 424/70.12 |
| 6,294,159 B1* | 9/2001 | Reich | A61K 8/585 424/70.1 |
| 2011/0052521 A1* | 3/2011 | Tanaka | A61K 8/062 424/70.12 |
| 2015/0197625 A1* | 7/2015 | Osawa | C08K 5/5419 524/266 |

FOREIGN PATENT DOCUMENTS

| | | |
|---|---|---|
| EP | 0 463 431 A2 | 1/1992 |
| JP | 63-125530 A | 5/1988 |
| JP | 5-32788 A | 2/1993 |
| JP | 7-70327 A | 3/1995 |
| JP | 2003-24707 A | 1/2003 |
| JP | 2004-217816 A | 8/2004 |
| JP | 2015-134846 A | 7/2015 |

* cited by examiner

*Primary Examiner* — Margaret G Moore
(74) *Attorney, Agent, or Firm* — Birch, Stewart, Kolasch & Bird, LLP

(57) ABSTRACT

The present invention aims to provide an emulsion composition of an organopolysiloxane which has enhanced stability in a water-soluble solvent. The invention provides an organosilicone emulsion composition comprising
(A) 100 parts by mass of an organopolysiloxane having a viscosity of at least 500 Pa·s at 25° C.;
(B) 1 to 50 parts by mass of a polyether group-containing organosiloxysilicate;
(C) 1 to 50 parts by mass of an organopolysiloxane having polyoxyalkylene residues at the both terminals;
(D) 1 to 50 parts by mass of a nonionic surfactant; and
(E) 10 to 1,000 parts by mass of water.

10 Claims, No Drawings

ORGANOSILICONE EMULSION COMPOSITION

TECHNICAL FIELD

The present invention relates to an organosilicone emulsion composition. In particular, it relates to an emulsion composition of a high-viscosity organopolysiloxane which has good stability in water-soluble solvents.

BACKGROUND

Organopolysiloxanes have been used as textile treatment agents, release agents, water repellents and in cosmetics, on account of their ability to impart smoothness and water repellency to substrates. Among them, high-viscosity organopolysiloxanes are quite effective for imparting smoothness. With ever increasing environmental concerns, there is an increasing trend to use aqueous treatment agents. There is also an increasing demand for stable emulsions of high-viscosity organopolysiloxanes. Some aqueous treatment agents contain a water-soluble solvent, and there is a need for an emulsion of a high-viscosity organopolysiloxane which is stable even in such a solvent. Several methods for preparing a high-viscosity organopolysiloxane emulsion with good stability are known from Patent Documents 1 to 3 mentioned below. However, the emulsions obtained by the methods of Patent Documents 1 to 3 have poor stability in water-soluble solvents. In addition, the methods of Patent Documents 1 to 3 require a special emulsifying technique or device, and are therefore of limited use. Patent Document 4 describes that an organosilicone emulsion composition comprising a high-viscosity organopolysiloxane and a polyether group-containing organosiloxysilicate shows improved stability of the emulsion.

LIST OF REFERENCES

Patent Document 1: JP-A H05-032788/1993
Patent Document 2: JP-A H07-070327/1995
Patent Document 3: JP-A S63-125530/1988
Patent Document 4: JP-A 2015-134846

SUMMARY OF THE INVENTION

Problems to be Solved by the Invention

The stability of the emulsion described in Patent Document 4 is unsatisfactory in admixture with a water-soluble solvent. To address these problems, the present invention aims to provide an emulsion composition of an organopolysiloxane which has enhanced stability in a water-soluble solvent.

Means to Solve the Problems

In order to achieve the above objective, the present inventor undertook extensive investigations, and has found that an emulsion having improved stability in a water-soluble solvent can be obtained by incorporating an organopolysiloxane having polyoxyalkylene residues at the both terminals in an organosilicone emulsion composition comprising a high-viscosity organopolysiloxane and a polyether group-containing organosiloxysilicate. This finding led to the present invention.

Thus, the invention provides an organosilicone emulsion composition comprising (A) 100 parts by mass of an organopolysiloxane having a viscosity of at least 500 Pa·s at 25° C.;
(B) 1 to 50 parts by mass of a polyether group-containing organosiloxysilicate;
(C) 1 to 50 parts by mass of an organopolysiloxane having polyoxyalkylene residues at the both terminals;
(D) 1 to 50 parts by mass of a nonionic surfactant; and
(E) 10 to 1,000 parts by mass of water.

Effects of the Invention

The present organosilicone emulsion composition provides an emulsion having good stability in a water-soluble solvent.

DETAILED DESCRIPTION

The present invention will be described in more detail below.

(A) High-Viscosity Organopolysiloxane

Component (A) is an organopolysiloxane having a viscosity of at least 500 Pa·s, preferably at least 1,000 Pa·s at 25° C. If the viscosity at 25° C. is less than the lower limit, sufficient characteristics are not attained when the organopolysiloxane emulsion composition is used as a surface coating or release agent. The viscosity of the organopolysiloxane, as determined in a 30% by mass solution in toluene at 25° C., is preferably up to 200 Pa·s, in particular up to 100 Pa·s. The viscosity herein is measured by a rotational viscometer. The organopolysiloxane may be any of a linear, branched, cyclic or three-dimensional network structure, in so far as it has a viscosity as described above. Preferably, the organopolysiloxane is linear.

The organopolysiloxane may be preferably represented by the general formula (I) shown below:

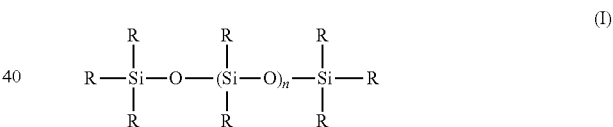

(I)

wherein R is, independently at each occurrence, a substituted or unsubstituted, monovalent hydrocarbon group having 1 to 20 carbon atoms, an alkoxy group having 1 to 6 carbon atoms, or a hydroxyl group; and n is an integer of from 500 to 10,000, with the proviso that n has a value such that the organopolysiloxane has a viscosity of at least 500 Pa·s at 25° C.

R is a substituted or unsubstituted, monovalent hydrocarbon group having 1 to 20 carbon atoms, preferably 1 to 6 carbon atoms, an alkoxy group having 1 to 6 carbon atoms, preferably 1 to 4 carbon atoms, or a hydroxyl group. Examples of the substituted or unsubstituted, monovalent hydrocarbon group include alkyl groups, such as methyl, ethyl, propyl, butyl, pentyl, hexyl, heptyl, octyl, nonyl, decyl, dodecyl, tetradecyl, hexadecyl, octadecyl, cyclopentyl, cyclohexyl and cycloheptyl groups; aryl groups, such as phenyl, benzyl, tolyl, xylyl and naphthyl groups; alkenyl groups, such as vinyl, allyl, butenyl and pentenyl groups; aralkyl groups, such as benzyl, phenylethyl and phenylpropyl groups; and those in which a part or all of the hydrogen atoms are substituted with, e.g., one or more halogen atoms (e.g., fluorine, bromine or chlorine atom), cyano, amino, epoxy or mercapto groups, for example, fluorine-substituted alkyl groups, such as —CF$_3$, —CH$_2$CF$_3$, —C$_2$H$_4$CF$_3$—, —$C_3H_6CF_3$, —$C_4H_8CF_3$, —$C_2F_5$, —$C_3F_7$, —$C_4F_9$, —$C_5F_{11}$, —$C_6F_{13}$, —$C_7F_{15}$, —$C_8F_{17}$ and —$C_9F_{19}$; amino-substituted alkyl groups, such as —$C_3H_6NH_2$ and —$C_3H_6NHC_2H_4NH_2$; epoxy-substituted alkyl groups, such as —$C_3H_6OCH_2HCH(O)CH_2$; and mercapto-substituted alkyl groups, such as —$C_3H_6SH$. Examples of the alkoxy group include methoxy, ethoxy, propoxy and butoxy groups. It is particularly preferable that at least 90% of R, as percentage relative to the total number of R groups, is a methyl group. When R is a hydroxyl or alkoxy group, it is preferably attached at one end or, preferably, both ends of the molecular chain.

(B) Polyether Group—Containing Organosiloxysilicate

Component (B) is a polyether group-containing organosiloxysilicate, and serves as an additive for enhancing the stability of the emulsion. An organosiloxysilicate is a polysiloxane composed of a silicate unit of the formula [$SiO_2$] (called Q unit) and one or more other organosiloxane units, i.e., M unit of the formula [$R'_3SiO_{1/2}$], T unit of the formula [$R'SiO_{3/2}$] and D unit of the formula [$R'_2SiO_{2/2}$]. Preferably, it is composed essentially of Q and M units. As used herein, a polyether group-containing organosiloxysilicate is an organosiloxysilicate having at least one polyether group attached to a silicon atom.

According to one embodiment of the invention, the organosiloxysilicate is composed essentially of [$SiO_{4/2}$] and [$R'_3SiO_{1/2}$] units. As used herein, "composed essentially of" is intended to mean that the compound comprise 25 to 75%, preferably 30 to 60%, of [$SiO_{4/2}$] units, and 23 to 75%, preferably 25 to 60%, of [$R'_3SiO_{1/2}$] units, based on the total number of the siloxane units (i.e., Q, M, T and D units). The molar ratio of [$R'_3SiO_{1/2}$] units to [$SiO_{4/2}$] units, i.e., [$R'_3SiO_{1/2}$]/[$SiO_{4/2}$] ratio, is preferably from 0.3 to 3, in particular from 0.4 to 2. If this ratio is too large or too small, the emulsion stability may be worse.

The organosiloxysilicate may further comprise D unit of the formula [$R'_2SiO_{2/2}$] and/or T unit of the formula [$R'SiO_{3/2}$]. The content of D and T units is preferably such that a total amount of D and T units is from 0 to 20% by mass, preferably 0 to 10% by mass, based on the total mass of the polyether group-containing organosiloxysilicate.

According to one embodiment of the invention, the polyether group-containing organosiloxysilicate may comprise at least one moiety represented by [$O_{1/2}R^2$] attached to the [$SiO_{4/2}$] unit. The [$O_{1/2}R^2$] moiety may be a hydroxyl group, an alkoxy group having 1 to 6 carbon atoms, or a polyether group-containing group of the formula (II) shown below with X being a single bond. In the M, T and D units, R' is, independently at each occurrence, an unsubstituted or substituted, monovalent hydrocarbon group having 1 to 12 carbon atoms, preferably 1 to 10 carbon atoms, more preferably 1 to 6 carbon atoms, an alkoxy group having 1 to 6 carbon atoms, preferably 1 to 4 carbon atoms, or a polyether group-containing group of the formula (II) shown below. As used herein, the polyether group-containing organosiloxysilicate comprises at least one polyether group-containing group of the formula (II) shown below:

$$—X—(OC_2H_4)_a(OC_3H_6)_b(OC_4H_8)_c—O—Y \quad (II)$$

wherein X is a single bond or an unsubstituted or substituted, divalent hydrocarbon group having 2 to 12 carbon atoms; Y is a hydrogen atom, an unsubstituted or substituted, monovalent hydrocarbon group having 1 to 20 carbon atoms, or a group of the formula —COR", wherein R" is an alkyl group having 1 to 10 carbon atoms, preferably 1 to 6 carbon atoms; a is an integer of from 1 to 50; b is an integer of from 0 to 30; and c is an integer of from 0 to 30. The parenthesized oxyethylene, oxypropylene and oxybutylene groups in the formula (II) may be sequenced at random or form a block unit.

In the formula (II) above, X is a single bond or an unsubstituted or substituted, divalent hydrocarbon group having 2 to 12 carbon atoms. Examples of the divalent hydrocarbon group include alkylene groups, such as methylene, ethylene, propylene (e.g., trimethylene, methylethylene), butylene (e.g., tetramethylene, methylpropylene), and hexamethylene groups. Among these, a single bond, propylene and butylene groups are preferred.

In the formula (II) above, Y is a hydrogen atom, an unsubstituted or substituted, monovalent hydrocarbon group having 1 to 20 carbon atoms, or a group of the formula —COR", wherein R" is an alkyl group having 1 to 10 carbon atoms, preferably 1 to 6 carbon atoms. Examples of the unsubstituted or substituted, monovalent hydrocarbon group having 1 to 20 carbon atoms include alkyl groups, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, cyclopentyl, cyclohexyl and cycloheptyl groups; aryl groups, such as a phenyl group; alkenyl groups, such as vinyl, allyl, butenyl and pentenyl groups; aralkyl groups, such as benzyl, phenylethyl and phenylpropyl groups; those in which a part of the hydrogen atoms are substituted with oxygen, such as an acetyl group; and those in which a part or all of the hydrogen atoms are substituted with one or more halogen atoms (e.g., fluorine, bromine or chlorine atom) or a cyano group, such as chloromethyl, chloropropyl, bromoethyl, trifluoropropyl and cyanoethyl groups. Among these, a hydrogen atom, methyl, butyl, dodecyl, tridecyl, tetradecyl, pentadecyl, hexadecyl, heptadecyl, octadecyl and acetyl groups are preferred for Y.

The subscript a is an integer of from 1 to 50, preferably from 3 to 30, b is an integer of from 0 to 30, preferably from 0 to 20, and c is an integer of from 0 to 30, preferably from 0 to 20.

R' is, independently at each occurrence, an unsubstituted or substituted, monovalent hydrocarbon group having 1 to 12 carbon atoms, preferably 1 to 10 carbon atoms, more preferably 1 to 6 carbon atoms, an alkoxy group having 1 to 6 carbon atoms, preferably 1 to 4 carbon atoms, or a polyether group-containing group of the formula (II) shown above. Examples of the unsubstituted or substituted, monovalent hydrocarbon group include alkyl groups, such as methyl, ethyl, propyl, butyl, pentyl, hexyl, heptyl, octyl, nonyl, decyl, dodecyl, cyclopentyl, cyclohexyl and cycloheptyl groups; aryl groups, such as a phenyl group; alkenyl groups, such as vinyl, allyl, butenyl and pentenyl groups; aralkyl groups, such as benzyl, phenylethyl and phenylpropyl groups; monovalent hydrocarbon groups in which a part or all of the hydrogen atoms are substituted with one or more halogen atoms (e.g., fluorine, bromine or chlorine atom) or a cyano group, such as chloromethyl, chloropropyl, bromoethyl, trifluoropropyl and cyanoethyl groups. Examples of the alkoxy groups include methoxy, ethoxy, propoxy and butoxy groups. Among these, a methyl group is particularly preferred.

Examples of the group of the formula (II) include
—$(OC_2H_4)_a$—O—$C_{10}H_{21}$,  —$(OC_2H_4)_a$—O—$C_{11}H_{23}$,
—$(OC_2H_4)_a$—O—$C_{12}H_{25}$,  —$(OC_2H_4)_a$—O—$C_{14}H_{29}$,
—$(OC_2H_4)_a$—O—$C_{16}H_{33}$,  —$(OC_2H_4)_a$—O—$C_{18}H_{37}$,
—$(OC_2H_4)_a(OC_3H_6)_b$—O—$C_{10}H_{21}$,  —$(OC_2H_4)_a(OC_3H_6)_b$—O—$C_{11}H_{23}$,  —$(OC_2H_4)_a(OC_3H_6)_b$—O—$C_{12}H_{25}$,  —$(OC_2H_4)_a(OC_3H_6)_b$—O—$C_{14}H_{29}$,  —$(OC_2H_4)_a(OC_3H_6)_b$—O—$C_{16}H_{33}$,  —$(OC_2H_4)_a(OC_3H_6)_b$—O—

$C_{18}H_{37}$, $-(OC_2H_4)_a-OC_6H_4-C_8H_{17}$, $-(OC_2H_4)_a-OC_6H_4-C_9H_{19}$, $-C_2H_4-(OC_2H_4)_a-O-H$, $-C_2H_4-(OC_2H_4)_a-O-CH_3$, $-C_2H_4-(OC_2H_4)_a-O-C_4H_9$, $-C_2H_4(OC_2H_4)_a-O-COCH_3$, $-C_3H_6-(OC_2H_4)_a-O-H$, $-C_3H_6-(OC_2H_4)_a-O-CH_3$, $-C_3H_6-(OC_2H_4)_a-O-C_4H_9$, $-C_3H_6-(OC_2H_{14})_a-O-COCH_3$, $-C_4H_8-(OC_2H_4)_a-O-H$, $-C_4H_8-(OC_2H_4)_a-O-CH_3$, $-C_4H_8-(OC_2H_4)_a-O-C_4H_9$, and $-C_4H_8-(OC_2H_4)_a-O-COCH_3$, in which a and b are as defined above. Among these, $-(OC_2H_4)_a-O-C_{10}H_{21}$, $-(OC_2H_4)_a-O-C_{11}H_{23}$, $-(OC_2H_4)_a-O-C_{12}H_{25}$, $-(OC_2H_4)_a-O-C_{14}H_{29}$, $-(OC_2H_4)_aO-C_{16}H_{33}$ and $-(OC_2H_4)_a-O-C_{18}H_{37}$ are preferred.

Component (B) may be a single compound or a mixture of two or more compounds.

Component (B) may have a polyether group content in the range of from 10 to 80% by mass, preferably from 15 to 60% by mass, based on the total mass of the polyether group-containing organosiloxysilicate. A polyether group content within this range is advantageous because it further improves the stability of the emulsion.

Component (B) preferably has a viscosity of from 0.1 to 1,000 Pa·s, preferably 0.2 to 500 Pa·s, at 25° C.

In the composition according to the invention, the amount of component (B) may be from 1 to 50 parts by mass, preferably from 3 to 40 parts by mass, more preferably from 5 to 30 parts by mass, relative to 100 parts by mass of component (A). Owing to the amount within the range described above, an emulsion having good stability can be obtained.

Polyether group-containing organosiloxysilicate (B) may be prepared by a conventional method known in the art, for instance, by a condensation reaction of an organosiloxysilicate having at least one hydroxyl group bonded to a silicon atom (silanol group) with a polyalkylene glycol, a polyalkylene glycol alkyl ether or a polyalkylene glycol alkyl ester, or by an addition reaction of an organosiloxysilicate having at least one Si—H group with a polyalkylene glycol having at least one unsaturated group. In particular, it is prepared preferably by a condensation of a (tri- or di-)methylsiloxysilicate having a silanol group with a polyalkylene glycol, a polyalkylene glycol alkyl ether or a polyalkylene glycol alkyl ester, or by an addition reaction between a methylsiloxysilicate having at least one silanol group and a polyalkylene glycol having at least one unsaturated group. Further preferred is a condensation product of a trimethylsiloxysilicate having at least one silanol group with a polyethylene glycol monoalkyl ether.

Examples of the organosiloxysilicate include trimethylsiloxysilicate, triethylsiloxysilicate and trimethylsiloxydimethyldisiloxysilicate, with trimethylsiloxysilicate and trimethylsiloxydimethyldisiloxy silicate being preferred. The organosiloxysilicate having at least one silanol group may be a compound in which at least one oxygen atom in Q unit $[SiO_{4/2}]$ of the organosiloxysilicate is replaced with a hydroxyl group, in which at least one substituent (R) bonded to a silicon atom in M unit $[R_3SiO_{1/2}]$ may be replaced with a hydroxyl group. Alternatively, the organosiloxysilicate having at least one silanol group may be a compound in which at least one substituent (R) bonded to a silicon atom in M unit $[R_3SiO_{1/2}]$ of the organosiloxysilicate is replaced with a hydroxyl group, in which at least one oxygen atom in Q unit $[SiO_{4/2}]$ may be replaced with a hydroxyl group.

Polyalkylene glycols, polyalkylene glycol alkyl ethers and polyalkylene glycol alkyl esters may be represented by the general formula (III) shown below:

$$H-(OC_2H_4)_a(OC_3H_6)_b(OC_4H_8)_c-O-Y \qquad (III)$$

wherein Y, a, b and c are as defined above. The parenthesized oxyethylene, oxypropylene and oxybutylene groups in the formula (III) may be sequenced at random or form a block unit. Among these, $H-(OC_2H_4)_a-O-C_{10}H_{21}$, $H-(OC_2H_4)_a-O-C_{12}H_{25}$, $H-(OC_2H_4)_a-O-C_{13}H_{27}$ and $H-(OC_2H_4)_a-O-C_{14}H_{29}$ are preferred. Two or more of such polyalkylene glycols may be subjected to condensation with an organosiloxysilicate having at least one silanol group.

An amount of the organosiloxysilicate having at least one silanol group and the amount of the polyalkylene glycol, the polyalkylene glycol alkyl ether or the polyalkylene glycol alkyl ester for the condensation may be such that a molar ratio of the hydroxyl group of the polyalkylene glycol or alkyl ether or alkyl ester derivative thereof to the silanol group of the organosilicate is from 0.5 to 3, more preferably from 0.6 to 2. If the molar ratio is less than the lower limit, little or no improvement in the emulsion stability will be attained. Even if the molar ratio exceeds the upper limit, the conversion rate will not change.

The condensation reaction may suitably be carried out in the presence of a catalyst, and the reaction proceeds at an elevated temperature. The catalyst may be typically selected from tin, zinc, zirconium, bismuth and iron compounds. In particular, examples include tin octylate, dioctyltin diacetate, dioctyltin dilaurate, dioctyltin diversatate, dibutyltin dilaurate, zinc octylate, zirconium octylate, bismuth octylate, iron octylate, and iron acetylacetonate. The condensation catalyst may be used in an amount of from 0.05 to 5% by mass, more preferably from 0.1 to 3% by mass, based on the total mass of the organosiloxysilicate having at least one silanol group and the polyalkylene glycol, polyalkylene glycol alkyl ether or polyalkylene glycol alkyl ester.

Although there is no particular limitation on reaction conditions, the condensation reaction may be preferably conducted at a pressure ranging from atmospheric pressure to a reduced pressure of about 100 Pa, at 30 to 150° C. for 1 to 300 hours, more preferably at 80 to 120° C. for 5 to 50 hours.

Examples of the organosiloxysilicate having at least one Si—H group include dimethylsiloxysilicate, dimethylsiloxytrimethylsiloxysilicate, dimethylsiloxydimethyldisiloxysilicate, and dimethylsiloxytrimethylsiloxydimethyldisiloxysilicate, with dimethylsiloxysilicate being preferred.

Polyalkylene glycols having at least one unsaturated group may be represented by the general formula (IV) shown below:

$$CH_2=CH-Z-(OC_2H_4)_a(OC_3H_6)_b(OC_4H_8)_c-O-Y \qquad (IV)$$

wherein Y, a, b and c are as defined above; and Z is a single bond or a substituted or unsubstituted, divalent hydrocarbon group having 1 to 10 carbon atoms. The parenthesized oxyethylene, oxypropylene and oxybutylene groups in the formula (IV) may be sequenced at random or form a block unit.

In the formula (IV), Z is a single bond or a substituted or unsubstituted, divalent hydrocarbon group having 1 to 10 carbon atoms, including, for example, an alkylene group, such as methylene, ethylene, propylene (e.g., trimethylene, methylethylene), butylene (e.g., tetramethylene, methylpropylene), and hexamethylene groups. Preferably, Z is a single bond or an unsubstituted divalent hydrocarbon group having 1 or 9 carbon atoms.

Among the polyalkylene glycols having at least one unsaturated group, polyethylene glycol monoallyl ethers and polyethylene glycol alkyl allyl ethers are preferred.

The organosiloxysilicate having at least one Si—H group and the polyalkylene glycol having at least one unsaturated group may be subjected to the addition reaction in relative amounts such that the molar ratio of the unsaturated group of the polyalkylene glycol to the Si—H group of the organosiloxysilicate is from 1 to 2.

The addition reaction may be suitably be carried out in the presence of a catalyst. Examples of the catalysts include those based on platinum group metals, such as chloroplatinic acid. The catalyst for the addition reaction may be used in an amount of from 0.0001 to 0.01% by mass, more preferably 0.0003 to 0.003% by mass, based on the total mass of the organosiloxysilicate having at least one Si—H group and the polyalkylene glycol having at least one unsaturated group.

Although there is no particular limitation on reaction conditions, the addition reaction may be preferably conducted under atmospheric pressure, at 30 to 130° C. for 1 to 24 hours, more preferably at 60 to 120° C. for 1 to 8 hours.
(C) Organopolysiloxane Having Polyoxyalkylene Residues at the Both Terminals The composition according to the invention may be characterized in that it comprises component (C) together with components (A) and (B) in respective amounts specified above, whereby the stability of the emulsion in a water-soluble solvent is improved. The organopolysiloxane having polyoxyalkylene residues at the both terminals is a compound in which a polyalkylene group attached to the silicon atom is at each of both terminals of the organopolysiloxane. The organcipolysiloxane may be linear or branched, preferably linear.

The organopolysiloxanes having polyoxyalkylene residues at the both terminals may be represented by the general formula (VI) shown below:

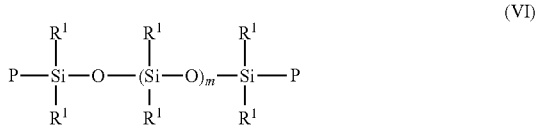

(VI)

wherein $R^1$ is, independently at each occurrence, a substituted or unsubstituted, monovalent hydrocarbon group having 1 to 20 carbon atoms, an alkoxy group having 1 to 6 carbon atoms, or a hydroxyl group; m is an integer of from 0 to 2,000; and P is a moiety represented by the general formula (VII) shown below:

(VII)

wherein X' is a single bond or an alkylene group having 1 to 10 carbon atoms, preferably 1 to 6 carbon atoms; a' is an integer of from 1 to 100; b' is an integer of from 0 to 50; c' is an integer of from 0 to 30; and Y' is a hydrogen atom, an unsubstituted or substituted, monovalent hydrocarbon group having 1 to 20 carbon atoms, preferably 1 to 18 carbon atoms, or a group of the formula —COR", wherein R" is an alkyl group having 1 to 10 carbon atoms, preferably 1 to 6 carbon atoms. The parenthesized oxyethylene, oxypropylene and oxybutylene groups in the formula (VII) may be sequenced at random or form a block unit.

Examples of the substituted or unsubstituted, monovalent hydrocarbon groups and the alkoxy groups for $R^1$ include those mentioned for the formula (I) of component (A). It is particularly preferable that at least 90% of $R^1$, as percentage relative to the total number of $R^1$ groups, is a methyl group.

In the general formula (VII), X' is a single bond or an alkylene group having 1 to 10 carbon atoms, preferably 1 to 6 carbon atoms. Example of the alkylene group include methylene, ethylene, propylene (e.g., trimethylene, methylethylene), butylene (e.g., tetramethylene, methylpropylene), and hexamethylene groups. Preferably, X' is a single bond, or propylene or butylene groups.

Y' is a hydrogen atom, an unsubstituted or substituted, monovalent hydrocarbon group having 1 to 20 carbon atoms, preferably 1 to 18 carbon atoms, or a group of the formula —COR". Examples of the unsubstituted or substituted, monovalent hydrocarbon group include alkyl groups, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, cyclopentyl, cyclohexyl and cycloheptyl groups; aryl groups, such as a phenyl group; alkenyl groups, such as vinyl, allyl, butenyl and pentenyl groups; aralkyl groups, such as benzyl, phenylethyl and phenylpropyl groups; those in which a part of the hydrogen atoms are substituted with oxygen, such as an acetyl group; and those in which a part or all of the hydrogen atoms are substituted with one or more halogen atoms (e.g., fluorine, bromine or chlorine atoms) or a cyano group, such as chloromethyl, chloropropyl, bromoethyl, trifluoropropyl and cyanoethyl groups. Examples of the group of the formula —COR" include —COMe, —COEt, —COnPr, —COiPr and —ConBu. Among these, a hydrogen atom, methyl, butyl, dodecyl, tridecyl, tetradecyl, pentadecyl, hexadecyl, heptadecyl, and octadecyl groups, and —COMe, —COEt, —COnPr, —COiPr and —ConBu are preferred for Y'.

The subscript a' is an integer of from 1 to 100, preferably from 10 to 60, and more preferably from 15 to 40; b' is an integer of from 0 to 50, preferably from 1 to 30; and c' is an integer of from 0 to 30, preferably from 0 to 20.

Examples of the moiety of formula (VII) include the examples of the group of the formula (II) in component (B). Preferably, it may be selected from —$C_3H_6$—($OC_2H_4$)$_{a'}$—($OC_3H_6$)$_{b'}$—OBu, —$C_3H_6$—($OC_2H_4$)$_{a'}$—OBu, —$C_3H_6$—($OC_2H_4$)$_{a'}$($OC_3H_6$)$_{b'}$—OMe, —$C_3H_6$—($OC_2H_4$)$_{a'}$—OMe, —$C_3H_6$—($OC_2H_4$)$_{a'}$($OC_3H_6$)$_{b'}$—OH, —$C_3H_6$—($OC_2H_4$)$_{a'}$—OH, —$C_3H_6$—($OC_2H_4$)$_{a'}$($OC_3H_6$)$_{b'}$OAc, and —$C_3H_6$—($OC_2H4$)$_{a'}$—OAc, wherein a' and b' are as defined above.

The subscript m is an integer of from 0 to 2,000, preferably form 20 to 1,000, more preferably from 40 to 700.

The amount of component (C) may be from 1 to 50 parts by mass, preferably from 3 to 40 parts by mass, more preferably from 6 to 35 parts by mass, relative to 100 parts by mass of component (A). An amount of component (C) less than the lower limit will diminish the stability of the emulsion in a water-soluble solvent. On the other hand, an amount of component (C) above the upper limit may detract from the characteristics of silicone in the composition.
(D) Nonionic Surfactant Component (D) is a nonionic surfactant which serves to emulsify and disperse the organopolysiloxane and the polyether group-containing organosiloxysilicate in water. Any nonionic surfactant known in the art may be used without any particular limitation. Examples of the nonionic surfactant include polyoxyethylene alkyl ethers, polyoxyethylene propylene alkyl ethers, polyoxyethylene alkyl phenyl ethers, and polyoxyethylene fatty acid esters. Among these, polyoxyethylene alkyl ethers, polyoxyethylene propylene alkyl ethers, and polyoxyethylene alkyl phenyl ethers are preferred in view of stability. Specific examples include polyoxyethylene octyl ether, polyoxyethylene nonyl ether, polyoxyethylene decyl ether, polyoxyethylenepropylene decyl ether, polyoxyethylene lauryl ether, polyoxyethylenepropylene lauryl ether, polyoxyethylene tridecyl ether, polyoxyethylenepropylene tridecyl ether, polyoxyethylene myristyl ether, polyoxyethylene cetyl ether, polyoxyethylene stearyl ether, polyoxyethylene octyl phenyl ether, polyoxyethylene nonyl phenyl ether, and polyoxyethylene styrenated phenyl ether. These emulsifiers may be used alone or in combination.

The amount of component (D) may be from 1 to 50 parts by mass, preferably from 2 to 40 parts by mass, more preferably from 3 to 30 parts by mass, relative to 100 parts by mass of component (A). An amount of component (D) less than the lower limit will make emulsification difficult. On the other hand, an amount of component (D) above the upper limit may detract from the characteristics of silicone in the composition.

According to one embodiment of the invention, the organosilicone emulsion composition contain water as component (E) in an amount of 10 to 1,000 parts by mass, preferably 30 to 300 parts by mass, relative to 100 parts by mass of component (A).

There is no particular limitation on methods for preparing the organosilicone emulsion composition. Components (A), (B) and (D) may be stirred to homogeneity using a planetary mixer, Shinagawa mixer or other mixers capable of mixing and stirring highly viscous materials, followed by gradual addition of water (E) to form a uniform emulsion. Then, the organopolysiloxane having polyoxyalkylene residues at the both terminals (C) may be added and uniformly mixed to obtain the organosilicone emulsion composition according to the invention. Alternatively, component (C) may be mixed with components (A), (B) and (D) before the adition of water (E).

The organosilicone emulsion composition preferably has a viscosity at 25° C. of 25 to 1,000 Pa·s, more preferably 30 to 500 Pa·s. If the viscosity is less than the lower limit, the stability of the emulsion may be poor. If the viscosity exceeds the upper limit, the workability of the emulsion may be adversely affected.

Preferably, the dispersed particles in the organosilicone emulsion composition has emulsified particles of a size of from 0.3 to 3.0 µm, more preferably from 0.4 to 2.5 µm. If the particle size is less than the lower lmit, the viscosity of the emulsion may be too high. If the particle size exceeds the upper limit, the stability of the emulsion may be poor. It is noted that the particle size of emulsions is determined with Particle Size Distribution Analyzer LA-920 commercially available from Horiba, Ltd.

The organosilicone emulsion composition has improved stability in a water-soluble solvent. A stable emulsion mixture can be obtained by mixing the organosilicone emulsion composition with a water-soluble solvent. As used herein, a water-soluble solvent is intended to mean a solvent that dissolves in water at a mass ratio of 1:1. Examples of the water-soluble solvent include alcohols, such as, methanol, ethanol, 1-propanol, isopropyl alcohol (IPA) and n-butanol; ketones, such as acetone and methyl ethyl ketone; and amides such as N,N-dimethylformamide. The proportion of the water-soluble solvent to be mixed may be suitably chosen depending on particular use.

The organosilicone emulsion composition has improved stability in a water-soluble solvent, and are therefore useful in a variety of fields, for instance, as surface coating agents, release agents, lubricants and gloss agents for a variety of substrates.

EXAMPLES

Examples and Comparative Examples are given below for illustrating the invention though the invention is not limited thereto. In the Examples, a viscosity was measured at 25° C. using a BM-type rotational viscometer, and a particle size was determined using Particle Size Distribution Analyzer LA-920 from Horiba, Ltd.

Synthesis Example 1

Synthesis of Polyether Group-Containing Organosiloxysilicate

A silanol group-containing organosiloxysilicate was used as a starting material, which had a formula $[(CH_3)_3SiO_{1/2}]_n[SiO_{4/2}]_m[O_{1/2}H]_r$, wherein the ratio (n:m) was 0.43: 0.54, with the OH group content being 0.08 mol/100 g, and the OH group being attached to Q unit.

A vacuum stripping system equipped with a stirrer and thermometer was charged with 5,610 g of a 71% by mass solution of the silanol group-containing organosiloxysilicate in toluene, 2,770 g of Sannonic SS120 (a mixture of HO—$(C_2H_4O)_{12}$—$C_{12}H_{25}$ and HO—$(C_2H_4O)_{12}$—$C_{14}H_{29}$, from Sanyo Chemical Industries, Ltd.) and 34 g of Neostann U-28 (tin octylate, from Nitto Kasei Co., Ltd.). Toluene was distilled out at 100° C. and 10 mmHg, followed by a condensation reaction for 5 hours to yield a pale-yellow opaque product, polyether group-containing organosiloxysilicate 1. The product thus obtained had a viscosity of 40 Pa·s at 25° C., a volatile content of 0.5% by mass as measured after heating at 105° C. for 3 hours, and a polyether group content of 37% by mole.

Example 1

A 2-L planetary mixer was charged with (A) 100 parts by mass of dimethylpolysiloxane having a gum-like viscosity of at least 1,000 Pa·s and a viscosity in a 30% by mass solution in toluene of 5,000 mPa·s, (B) 14 parts by mass of polyether group-containing organosiloxysilicate 1 as obtained in Syntheris Example 1, and (D) 24 parts by mass of Sannonic SS120 (a mixture of HO—$(C_2H_4O)_{12}$—$C_{12}H25$ and HO—$(C_2H_4O)_{12}$—$C_{14}H_{29}$, from Sanyo Chemical Industries, Ltd.), which were mixed uniformly. Then, (E) 62 parts by mass of water was added, and the mixture was stirred and emulsified to yield emulsion A, which was a uniform white pasty emulsion containing particles of a size of 1.6 µm and had a viscosity of 38 Pa·s.

To 200 parts by mass of emulsion A were added (C) 8.5 parts by mass of polyoxyalkylene-terminated organopolysiloxane of the formula $PMe_2SiO—(SiMe_2O)_{60}—SiMe_2P$, wherein P is —$C_3H_6$—$(OC_2H_4)_{23}(OC_3H_6)_{23}$—OBu. The resulting mixture was mixed with a disperser (HOMOGENIZING DISPER, from PRIMIX Corp.) at 2,000 rpm for 30 minutes to yield an organosilicone emulsion composition, which was a uniform white pasty emulsion containing particles of a size of 1.6 µm and had a viscosity of 40 Pa·s. To 200 parts by mass of the organosilicone emulsion composition was added 150 parts by mass of IPA, and was mixed with a disperser (HOMOGENIZING DISPER, from PRIMIX) at 1,500 rpm for 1 minute to yield an emulsion mixture. This emulsion mixture was stable without causing separation, after storage at room temperature for 1 month.

Example 2

The procedures of Example 1 were repeated, except that the amount of component (C) was changed to 17 parts by mass to yield an organosilicone emulsion composition, which was a uniform white pasty emulsion containing particles of a size of 1.6 μm and had a viscosity of 43 Pa's. Then, IPA was added to the organosilicone emulsion composition as in Example 1 to prepare an emulsion mixture for evaluation of stability. The emulsion mixture was stable without causing separation, after storage at room temperature for 1 month.

Example 3

The procedures of Example 1 were repeated, except that the amount of component (C) was changed to 35 parts by mass to yield an organosilicone emulsion composition, which was a uniform white pasty emulsion containing particles of a size of 1.6 μm and had a viscosity of 46 Pa·s. Then, IPA was added to the organosilicone emulsion composition as in Example 1 to prepare an emulsion mixture for evaluation of stability. The emulsion mixture was stable without causing separation, after storage at room temperature for 1 month.

Comparative Example 1

An emulsion was prepared as in Example 1, but without the addition of component (C). Then, IPA was added to the emulsion as in Example 1 to prepare an emulsion mixture for evaluation of stability. The emulsion mixture caused separation after storage at room temperature for 1 day.

Comparative Example 2

An emulsion was prepared as in Example 1, except that 8.5 parts by mass of the above-mentioned surfactant, Sannonic SS120, was added in place of component (C), followed by mixing with a disperser (HOMOGENIZING DISPER, from PRIMIX) at 2,000 rpm for 30 minutes to yield an emulsion. Then, 150 parts by mass of IPA were added to the emulsion to prepare an emulsion mixture of the same concentration as in Example 1 for evaluation of stability. The emulsion mixture caused separation after storage at room temperature for 3 days.

Comparative Example 3

The procedures of Comparative Example 2 were repeated, except that the amount of Sannonic SS120 was changed to 17 parts by mass to yield an emulsion. Then, 150 parts by mass of IPA were added to the emulsion to prepare an emulsion mixture of the same concentration as in Example 1 for evaluation of stability. The emulsion mixture caused separation after storage at room temperature for 3 days.

Comparative Example 4

The procedures of Comparative Example 2 were repeated, except that the amount of Sannonic SS120 was changed to 35 parts by mass to yield an emulsion. Then, 150 parts by mass of IPA was added to the emulsion to prepare an emulsion mixture of the same concentration as in Example 1 for evaluation of stability. The emulsion mixture caused separation after storage at room temperature for 5 days.

INDUSTRIAL APPLICABILITY

The organosilicone emulsion composition according to the invention has good storage stability even in a water-soluble solvent, and is therefore useful in a variety of fields, for instance, as surface coating agents, release agents, lubricants and gloss agents for a variety of substrates.

The invention claimed is:
1. A mixture comprising:
(1) an organosilicone emulsion composition comprising
(A) 100 parts by mass of an organopolysiloxane having a viscosity of at least 500 Pa s at 25 degrees C.,
(B) 1 to 50 parts by mass of an organosiloxy silicate having at least one polyether group
(C) 1 to 50 parts by mass of a linear organopolysiloxane having polyoxyalkylene residues at both terminals,
(D) 1 to 50 parts by mass of a nonionic surfactant and
(E) 10 to 1,000 parts by mass of water,
and
(2) a water-soluble solvent selected from methanol, ethanol, 1-propanol, isopropyl alcohol (IPA), n-butanol, acetone, methyl ethyl ketone and N,N-dimethylformamide.
2. The mixture according to claim 1, wherein component (C) is represented by the following general formula (VI),

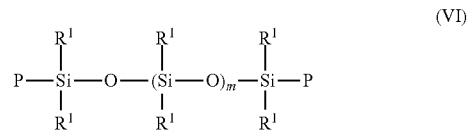

wherein $R^1$ is, independently of each other, an unsubstituted or substituted, monovalent hydrocarbon group having 1 to 20 carbon atoms, an alkoxy group having 1 to 6 carbon atoms or a hydroxy group, m is an integer of from 0 to 2000, and P is represented by the following general formula (VII):

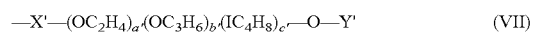

wherein X' is a single bond or an alkylene group having 1 to 10 carbon atoms, a' is an integer of from 1 to 100, b' is an integer of from 0 to 50, c' is an integer of from 0 to 30, Y' is a hydrogen atom, an unsubstituted or substituted, monovalent hydrocarbon group having 1 to 20 carbon atoms or —COR", and R" is an alkyl group having 1 to 10 carbon atoms, and the parenthesized oxyethylene, oxypropylene and oxybutylene groups in the formula (VII) may be sequenced at random or form a block unit.
3. The mixture according to claim 1 or 2, wherein component (A) is an organopolysiloxane represented by the following general formula (I):

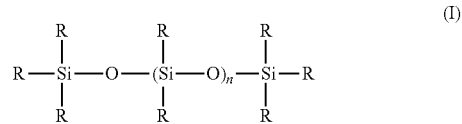

wherein R is, independently of each other, an unsubstituted or substituted, monovalent hydrocarbon group having 1 to 20 carbon atoms, an alkoxy group having 1 to 6 carbon atoms or a hydroxy group, and n is an integer of from 500 to 10,000.
4. The mixture according to claim 1, wherein an organosiloxy silicate moiety in component (B) comprises $SiO_{4/2}$ units and $R'_3SiO_{1/2}$ units, wherein a percentage of the number of $SiO_{4/2}$ units is 25 to 75% and a percentage of the number of $R'_3SiO_{1/2}$ units is 23 to 75%, based on the total number of the siloxane units, and wherein the organosiloxy silicate moiety comprises at least one $O_{1/2}R^2$ unit attached to $SiO_{4/2}$ unit;

wherein R' is, independently of each other, an unsubstituted or substituted, monovalent hydrocarbon group having 1 to 12 carbon atoms, an alkoxy group having 1 to 6 carbon atoms, or a group represented by the general formula (II):

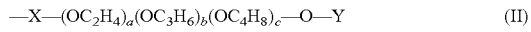
—X—$(OC_2H_4)_a(OC_3H_6)_b(OC_4H_8)_c$—O—Y    (II)

wherein X is a single bond or an unsubstituted or substituted, divalent hydrocarbon group having 2 to 12 carbon atoms, Y is a hydrogen atom, an unsubstituted or substituted, monovalent hydrocarbon group having 1 to 20 carbon atoms or —COR", R" is an alkyl group having 1 to 10 carbon atoms, a is an integer of from 1 to 50, b is an integer of from 0 to 30, c is an integer of from 0 to 30, and the parenthesized oxyethylene, oxypropylene and oxybutylene groups in the formula (II) may be sequenced at random or form a block unit, $O_{1/2}R^2$ unit is a hydroxy group, an alkoxy group having 1 to 6 carbon atoms or the group represented by the formula (II) with X being a single bond, and provided that the organosiloxy silicate has at least one polyether-containing group represented by the formula (II).

5. The mixture according to claim 1, wherein component (B) is a condensation product of an organosiloxy silicate having at least one hydroxy group bonded to a silicon atom with a polyalkylene glycol, a polyalkylene glycol alkyl ether or a polyalkylene glycol alkyl ester.

6. The mixture according to claim 5, wherein the polyalkylene glycol, the polyalkylene glycol alkyl ether and the polyalkylene glycol alkyl ester are represented by the following formula (III):

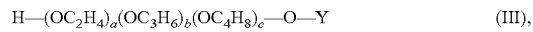
H—$(OC_2H_4)_a(OC_3H_6)_b(OC_4H_8)_c$—O—Y    (III), wherein Y, a, b and c are as defined above and the parenthesized oxyethylene, oxypropylene and oxybutylene groups in the formula (III) may be sequenced at random or form a block unit.

7. The mixture according to claim 6, wherein the polyalkylene glycol alkyl ether is polyethylene glycol monoalkyl ether.

8. The mixture according to claim 1, wherein component (B) is an addition product of an SiH group-containing organosiloxy silicate with a polyalkylene glycol having an unsaturated group.

9. The mixture according to claim 8, wherein the polyalkylene glycol having an unsaturated group is represented by the following general formula (IV):

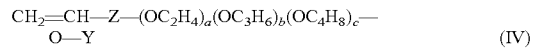
$CH_2$=CH—Z—$(OC_2H_4)_a(OC_3H_6)_b(OC_4H_8)_c$—O—Y    (IV)

wherein Y, a, b and c are as defined above, Z is a single bond or a divalent hydrocarbon group having 1 to 10 carbon atoms, and the parenthesized oxyethylene, oxypropylene and oxybutylene groups in the formula (IV) may be sequenced at random or form a block unit.

10. The mixture according to claim 1, wherein the water-soluble solvent is selected from methanol, ethanol, 1-propanol, isopropyl alcohol (IPA) and n-butanol.

* * * * *